US00PP24581P2

(12) United States Plant Patent
Zaiger et al.

(10) Patent No.: US PP24,581 P2
(45) Date of Patent: Jul. 1, 2014

(54) PEACH TREE NAMED 'FIRE GEM'

(50) Latin Name: *Prunus persica*
Varietal Denomination: Fire Gem

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 34 days.

(21) Appl. No.: 13/694,503

(22) Filed: Dec. 7, 2012

(51) Int. Cl.
*A01H 5/00* (2006.01)

(52) U.S. Cl.
USPC ..... Plt./197

(58) Field of Classification Search
CPC .. A01H 5/0868; A01H 5/0856; A01H 5/0837
USPC ..... Plt./197
See application file for complete search history.

*Primary Examiner* — Kent L Bell

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Being a regular and productive bearer of large size fruit.
3. Fruit with a high degree of attractive dark red skin color.
4. Firm, yellow flesh with good flavor and eating quality.
5. Fruit being relatively uniform in size throughout the tree.

1 Drawing Sheet

Botanical designation: *Prunus persica.*
Variety denomination: 'Fire Gem'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach trees, which are known to us, and mentioned herein, 'Vista' Peach (U.S. Plant Pat. No. 9,549), 'Super Rich' Peach (U.S. Plant Pat. No. 9,860) and our proprietary non-patented peach seedling selections '21LD51' and '7HB287'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from open pollinated seed collected from our proprietary seedling selection '21LD51' peach (non-patented). '21LD51' peach (non-patented) originated from a cross between 'Vista' Peach (U.S. Plant Pat. No. 9,549) and our proprietary seedling selection '7HB287' peach (non-patented). A large number of seed from this open pollinated seedling selection were grown on their own root system and budded to older trees of 'Nemaguard' Rootstock (non-patented), to accelerate rapid fruit production. Under close and careful evaluation we recognized the desirable tree and fruit characteristics of the present variety and selected it in 1998 for further asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree (*Prunus persica*) is of large size, vigorous, upright growth and a regular and productive bearer of large size, firm, yellow flesh clingstone fruit. The fruit is further characterized by having good flavor and eating quality, having a high degree of attractive dark red skin color and being relatively uniform in size throughout the tree. In comparison to its seed parent '21LD51' peach (non-patented) the fruit of the new variety is firmer and approximately two days later in maturity with a higher degree of attractive dark red skin color. In comparison to the commercial variety 'Super Rich' Peach (U.S. Plant Pat. No. 9,860) the fruit of the new variety has firmer flesh, a higher degree of attractive dark red skin color and is approximately 5 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 12 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 12 year old specimens grown near Modesto, Calif., with color in accordance with Munsell Book of Color published in 1958.

Tree:

*Size*.—Large, usually pruned to 3 to 3.5 meters in height and width for economical harvesting of fruit.

*Vigor*.—Vigorous, growth of 1.5 to 2 meters in height the first growing season. Varies slightly with soil type, fertility of soil and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size.

*Bearer*.—Regular, has had adequate fruit set 11 consecutive years. No alternate bearing observed.

*Fertility*.—Self-fertile.

*Density*.—Medium dense, usually pruned to vase shape to increase air movement and sunlight to the center of the tree to enhance fruit color and health of fruit wood.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium. Average circumference 58.3 cm at 30.5 cm above ground on a 12 year old tree.

*Stocky*.—Medium stocky.

*Texture*.—Medium shaggy, roughness increases with age.

*Color*.—Varies from 2.5Y 6/2 to 2.5Y 6/4.

Branches:

*Size*.—Medium. Average circumference 18.7 cm at 1.2 meters above ground. Crotch angle approximately 35°, increases with crop load.

*Surface texture*.—New growth relatively smooth. Mature growth medium rough, roughness increases with age.

*Lenticels*.—Average number 40 in a 25.8 sq cm section. Average length 4.2 mm. Average width 1.4 mm. Color varies from 10YR 6/8 to 10YR 5/8.

*Color*.—New growth varies from 5GY 6/6 to 5R 3/6 where exposed to the sun. Mature growth varies from 7.5YR 3/4 to 10YR 3/6, varies with age of growth.

Leaves:

*Size*.—Medium to large. Average length 128.6 mm. Average width 37.8 mm.

*Form*.—Lanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins. Lower surface relatively smooth, small ridges created by midrib and pinnate venation. Both surfaces glabrous.

*Petiole*.—Average length 9.9 mm. Average width 1.4 mm. Longitudinally grooved. Surface — glabrous. Color varies from 5GY 3/4 to 5GY 3/6.

*Glands*.—Type — reniform. Size — medium. Average length 1.3 mm. Average diameter 0.9 mm. Number varies from 2 to 6, average number 4. Located primarily on base of leaf blade, and the upper portion of petiole. Color varies from 2.5GY 6/6 to 5GY 6/6.

*Stipules*.—Average number 2. Average length 7.9 mm. Margin — pectinate. Color varies from 5GY 6/6 to 5R 3/8.

*Color*.—Upper surface varies from 5GY 3/2 to 7.5GY 3/4. Lower surface varies from 5GY 4/4 to 7.5GY 2/2. Midvein color varies from 2.5GY 7/4 to 2.5GY 6/4.

Flower buds:

*Size*.—Large. Average length 18.5 mm. Average diameter 12.0 mm.

*Hardiness*.—Hardy with respect to California winters.

*Form*.—Conical, becoming elongated before opening.

*Pedicel*.—Average length 4.7 mm. Average width 1.0 mm. Color varies from 2.5GY 7/6 to 2.5GY 6/6.

*Color*.—Varies from 5RP 8/6 to 7.5RP 7/8.

Flowers:

*Blooming period*.—Date of First Bloom Feb. 16, 2012. Date of Petal Fall Feb. 27, 2012, varies slightly with climatic conditions.

*Size*.—Large, showy. Average height 20.8 mm. Average diameter 49.9 mm.

*Petals*.—Normally 5, alternately arranged to sepals. Size — large. Average length 25.5 mm. Average width 22.5 mm. Form — nearly globose, base narrows at point of attachment. Margin — sinuate. Color varies from 7.5RP 9/2 to 5RP 7/6, fades with age of flower. Both upper and lower surfaces glabrous.

*Sepals*.—Normally 5, alternately arranged to petals. Size — large. Average length 6.2 mm. Average width 5.2 mm. Form — triangular, apex rounded. Margin — entire. Surface — upper surface glabrous, lower surface pubescent. Color — upper surface varies from 5GY 4/4 to 7.5R 3/2. Lower surface varies from 7.5R 3/2 to 7.5R 2/2.

*Stamens*.—Average number per flower 40, varies from 39 to 42. Average filament length 15.3 mm. Filament color varies from N 9.5/ (white) to 5RP 5/10. Anther color varies from 5Y 9/2 to 7.5R 3/10.

*Pollen*.—Self-fertile. Color varies from 10YR 7/10 to 2.5Y 7/12.

*Pistil*.—Normally 1. Surface — pubescent. Average length 20.1 mm. Position of stigma average of 1.0 mm above anthers. Color varies from 7.5Y 8/6 to 10Y 8/6.

*Fragrance*.—Slight aroma.

*Color*.—Varies from 5RP 8/4 to 5RP 7/6.

*Number flowers per flower bud*.—Normally one.

*Pedicel*.—Average length 5.3 mm. Average width 1.1 mm. Color varies from 2.5GY 5/6 to 2.5GY 6/6.

Fruit:

*Maturity when described*.—Firm ripe.

*Date of first picking*.—May 17, 2012.

*Date of last picking*.—May 24, 2012, varies slightly with climatic conditions.

*Size*.—Large. Average diameter 66.5 mm. Average transversely in suture plane 75.8 mm. Average weight 209.4 grams, average weight varies slightly with fertility of the soil, amount of thinning and climatic conditions.

*Form*.—Globose.

*Suture*.—Smooth to slightly lipped, extends from base to apex.

*Ventral surface*.—Nearly smooth.

*Apex*.—Slightly retuse.

*Base*.—Retuse.

*Stem cavity*.—Rounded to slightly elongated in suture plan. Average depth 5.4 mm. Average diameter 6.8 mm.

Stem:

*Size*.—Small to medium. Average length 10.0 mm. Average diameter 3.6 mm.

*Color*.—Varies from 5GY 6/8 to 5GY 5/8.

Flesh:

*Ripens*.—Evenly.

*Texture*.—Firm, meaty, crisp.

*Fibers*.—Few, small, tender.

*Firmness*.—Good, holds firm on the tree 8 to 10 days after maturity.

*Aroma*.—Moderate.

*Amydgalin*.—Undetected.

*Eating quality*.—Good.

*Flavor*.—Good.

*Juice*.—Moderate amount, enhances flavor.

*Brix*.—Average Brix 12.0°, varies slightly with amount of fruit per tree and climatic conditions.

*Color*.—Varies from 10YR 7/8 to 10YR 7/10, with areas of 7.5R 4/10 near the skin.

*Pit cavity*.—Average length 33.0 mm. Average width 28.0 mm. Average depth 12.4 mm. Color varies from 2.5Y 6/8 to 10YR 5/8.

Skin:

*Thickness*.—Medium.

*Surface*.—Smooth to slightly waffled.

*Pubescence*.—Short, moderate amount.

*Tendency to crack*.—None.

*Color*.—Ground color varies from 2.5Y 8.5/8 to 2.5Y 8/10. Overspread with 2.5YR 2/4 to 7.5R 2/4.

*Tenacity*.—Tenacious to flesh.

*Astringency*.—Undetected.

Stone:

*Type*.—Clingstone.

*Size*.—Large. Average length 31.7 mm. Average width 26.4 mm. Average thickness 22.8 mm.

*Form*.—Ovoid.

*Base*.—Varies from flat to slightly rounded.

*Apex*.—Pointed, average length 1.3 mm.

*Surface*.—Pitted throughout, pits vary from rounded to elongated.

*Sides*.—Unequal, one side extending further from suture plane.

*Ridges*.—Small ridges extending from base to apex.

*Tendency to split*.—Very slight.

*Color*.—Varies from 10YR 6/6 to 7.5YR 6/6 when dry.

Kernel:

*Size*.—Medium to large. Average length 17.4 mm. Average width 10.4 mm. Average depth 8.3 mm.

*Form*.—Ovate.

*Viability*.—Non-viable, incomplete embryo development.

*Skin color*.—Varies from 7.5Y 9/4 to 10Y 9/2.

Use:

*Dessert*.—Market — local and long distance.

Keeping quality: Good, held firm in cold storage at 38° to 42° F. for 3 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

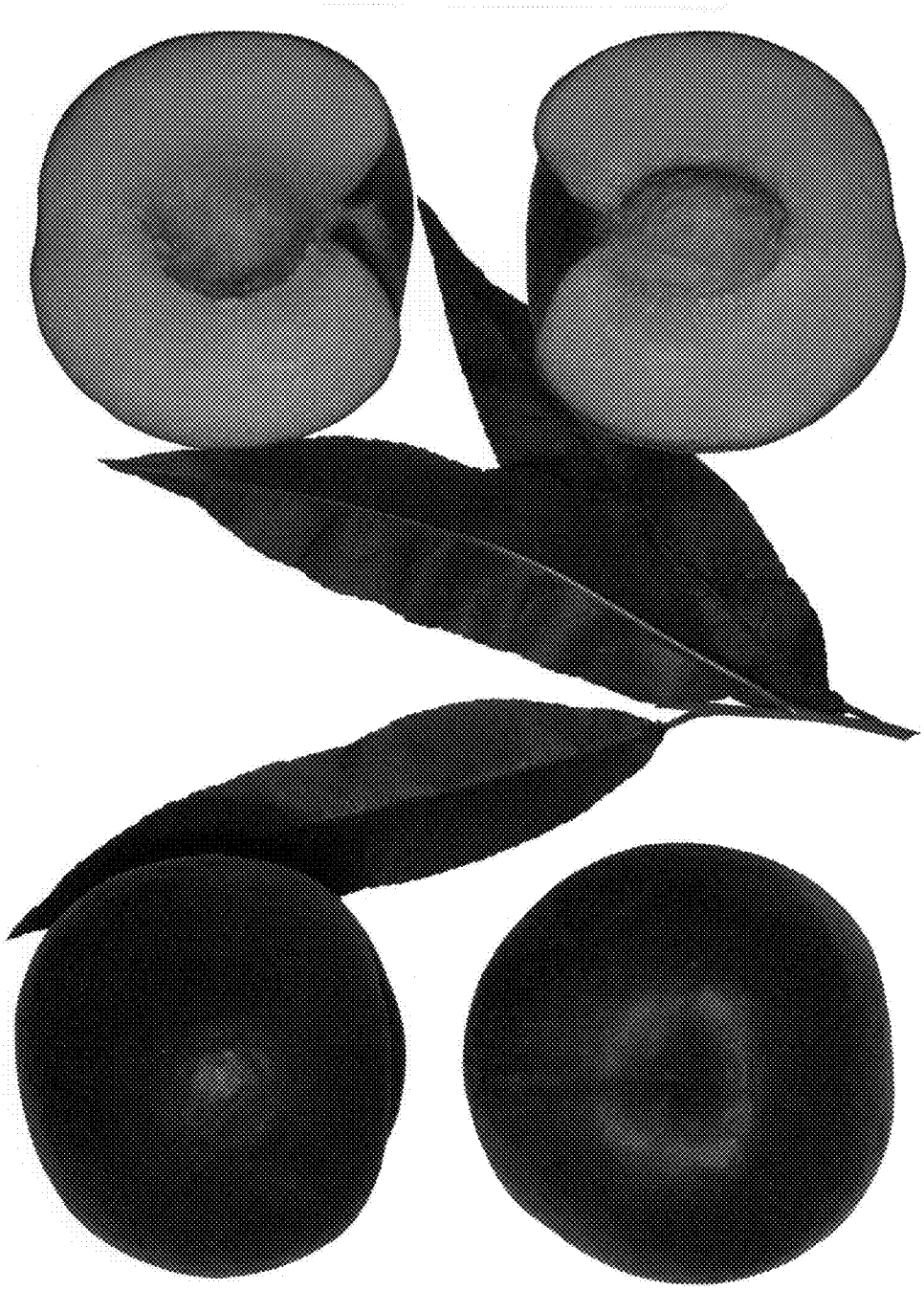

* * * * *